United States Patent
Chester et al.

(10) Patent No.: US 6,310,265 B1
(45) Date of Patent: Oct. 30, 2001

(54) ISOMERIZATION OF PARAFFINS

(75) Inventors: Arthur W. Chester, Cherry Hill; David C. Calabro, Princeton Junction; Sandeep S. Dhingra, Robbinsville, all of NJ (US); Jean W. Beeckman, Columbia, MD (US); Timothy J. Fiebig, Elmer; Glenn R. Sweeten, Mickleton, both of NJ (US); Terry E. Helton, Glen Mills, PA (US); Charles T. Kresge, Midland, MI (US); Richard F. Socha, Newtown, PA (US); Simon C. Weston, Voorhees, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/432,006

(22) Filed: Nov. 1, 1999

(51) Int. Cl.⁷ .................................................. C07C 5/22
(52) U.S. Cl. ......................... 585/739; 585/750; 585/751
(58) Field of Search .................................. 585/739, 750, 585/751

(56) References Cited

U.S. PATENT DOCUMENTS

| | | | |
|---|---|---|---|
| 3,354,078 | 11/1967 | Miale et al. | 208/120 |
| 4,419,220 | 12/1983 | LaPierre et al. | 208/111 |
| 4,919,788 | 4/1990 | Chen et al. | 208/59 |
| 6,049,018 | * 4/2000 | Calabro et al. | 585/446 |

OTHER PUBLICATIONS

"Superactive Crystalline Aluminosilicate Hydrocarbon Catalysts," P.B. Weisz, et al., Journal of Catalysis, 4, pp. 527–529, 1965.

"Catalysis by Crystalline Aluminosilicates," J.N. Miale, et al., Journal of Catalysis, 6, pp. 278–287, 1966.

"Chemical and Physical Properties of the ZSM–5 Substitutional Series," D.H. Olson, et al., Journal of Catalysis 61, pp. 390–396, 1980.

* cited by examiner

Primary Examiner—Bekir L. Yildirim

(57) ABSTRACT

This invention relates to a process for isomerizing paraffins comprising the step of contacting a feed containing paraffins with a catalyst comprising a synthetic porous crystalline material, designated MCM-68, which exhibits a distinctive X-ray diffraction pattern and has a unique crystal structure which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

10 Claims, No Drawings

ISOMERIZATION OF PARAFFINS

FIELD OF THE INVENTION

This invention relates to the isomerization of paraffins and particularly the hydroisomerization of n-paraffins.

BACKGROUND OF THE INVENTION

The isomerization of paraffins is an important reaction in both fuels and lubes refining in providing a mechanism for removing waxy components in the feed while minimizing cracking of these components to materials boiling outside the fuel and lube range. In fuels refining, paraffin isomerization is also used to produce high octane, branched paraffins to compensate for the octane deficit resulting from the removal or reduction of lead and aromatic components from the gasoline pool. Certain zeolites have been found to be good isomerization catalysts, particularly when impregnated with noble metals. For example, U.S. Pat. Nos. 4,419,220 and 4,919,788 disclose the use of zeolite beta as a paraffin isomerization catalyst. It has now been found that the recently discovered zeolite designated MCM-68 has activity for the isomerization of paraffins, particularly when steamed to a low acid activity (alpha) and impregnated with a hydrogenation metal, such as platinum.

SUMMARY OF THE INVENTION

According to the invention, there is provided a process for isomerizing paraffins comprising the step of contacting a feed containing paraffins with a catalyst comprising a porous crystalline material, MCM-68, which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10membered ring channels is twice the number of 12-membered ring channels.

Preferably, the contacting step is conducted in the presence of hydrogen and the catalyst contains a hydrogenation metal, most preferably a noble metal.

DETAILED DESCRIPTION OF THE INVENTION

The paraffin isomerization process of the invention employs the synthetic porous crystalline material MCM68, which is a single crystalline phase which has a unique 3-dimensional channel system comprising at least one channel system, in which each channel is defined by a 12-membered ring of tetrahedrally coordinated atoms, and at least two further independent channel systems, in which each channel is defined by a 10-membered ring of tetrahedrally coordinated atoms, wherein the number of unique 10-membered ring channels is twice the number of 12-membered ring channels. The normal crystalline form of MCM-68 contains one 12-membered ring channel system and two 10-membered ring channel systems, in which the channels of each system extend perpendicular to the channels of the other systems and in which the 12-ring channels are generally straight and the 10-ring channels are tortuous (sinusoidal).

MCM-68 can be prepared in essentially pure form with little or no detectable impurity crystal phases and, in its calcined form, has an X-ray diffraction pattern which is distinguished from the patterns of other known as-synthesized or thermally treated crystalline materials by the lines listed in Table 1 below. In its as-synthesized form, the crystalline MCM-68 material of the invention has an X-ray diffraction pattern which is distinguished from the patterns of other known as-synthesized or thermally treated crystalline materials by the lines listed in Table 2 below.

TABLE 1

| d(Å) | Relative Intensity [100 × I/I(o)] |
| --- | --- |
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW-W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |
| 3.40 +/− 0.10 | W |
| 3.24 +/− 0.09 | W |
| 2.90 +/− 0.08 | VW |

TABLE 2

| d(Å) | Relative Intensity [100 × I/I(o)] |
| --- | --- |
| 13.56 +/− 0.39 | VW |
| 12.93 +/− 0.37 | M-S |
| 10.92 +/− 0.31 | W |
| 10.16 +/− 0.29 | VW-W |
| 9.15 +/− 0.26 | VW-W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units, and the relative intensities of the lines, I/$I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

MCM-68 has a composition involving the molar relationship:

$$X_2O_3:(n)YO_2,$$

wherein X is a trivalent element, such as aluminum, boron, iron, indium, and/or gallium, preferably aluminum; Y is a tetravalent element such as silicon, tin, titanium and/or germanium, preferably silicon; and n is at least about 5, such as 5 to 100,000, and usually from about 8 to about 50. In the as-synthesized form, the material has a formula, on an anhydrous basis and in terms of moles of oxides per n moles of $YO_2$, as follows:

$$(0.1–2)M_2O:(0.2–2)Q:X_2O_3:(n)YO_2$$

wherein M is an alkali or alkaline earth metal, and Q is an organic moiety. The M and Q components are associated with the material as a result of their presence during crystallization, and are easily removed by post-crystallization methods hereinafter more particularly described.

MCM-68 can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (Q), and water, said reaction mixture having a composition, in terms of mole ratios of oxides, within the following ranges:

| Reactants | Useful | Preferred |
|---|---|---|
| $YO_2/X_2O_3$ | at least 5 | 8–50 |
| $H_2O/YO_2$ | 10–1000 | 15–100 |
| $OH^-/YO_2$ | 0.05–2 | 0.1–0.5 |
| $M/YO_2$ | 0.05–2 | 0.1–0.5 |
| $Q/YO_2$ | 0.01–1 | 0.05–0.2 |

The organic directing agent Q used herein is selected from the novel dications N,N,N',N'-tetraalkylbicyclo[2.2.2]oct-7-ene-2,3:5,6-dipyrrolidinium dication and N,N,N',N'-tetraalkylbicyclo[2.2.2]octane-2,3:5,6-dipyrrolidinium dication which can be represented by the following formulae:

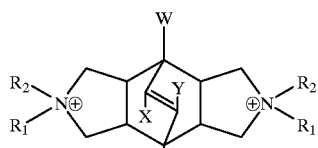

N,N,N',N'-tetraalkylbicyclo[2.2.2]oct-7-ene-2,3:5,6-dipyrrolidinium

-continued

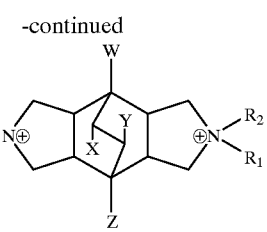

N,N,N',N'-tetraalkylbicyclo[2.2.2]octane-2,3:5,6-dipyrrolidinium where $R_1$, $R_2$ may be the same or different substituents selected from alkyl groups having 1 to 6 carbon atoms, phenyl and benzyl groups, or $R_1$ and $R_2$ may be linked as a cyclic group having 3 to 6 carbon atoms; and W, X, Y, Z may be the same or different substituents selected from hydrogen, alkyl groups having 1 to 6 carbon atoms, phenyl groups and halogens. In a preferred example, the organic directing agent is the N,N,N',N'-tetraethyl-exo,exo-bicyclo[2.2.2]oct-7-ene-2,3:5,6-dipyrrolidinium (Bicyclodiquat-$Et_4$) dication, having the formula $C_{20}H_{36}N_2^{++}$, which may be represented as follows:

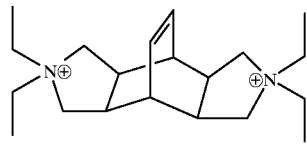

The source of the organic dication may be any salt which is not detrimental to the formation of the crystalline material of the invention, for example, the halide, e.g., iodide, or hydroxide salt.

The novel organic dications used to synthesize the MCM-68 of the invention can be prepared from, for example, exo,exo-bicyclo[2.2.2]oct-7-ene-2,3:5,6-tetracarboxylic dianhydride, which is a commercially available material. The dianhydride is initially reacted with ammonia or an amine to produce a diimide which is then reduced with $LiAlH_4$ to produce the diamine. The diamine can then be alkylated with an alkyl, phenyl or benzyl halide to produce the quaternary dication. Similarly, the bicyclooctane diquat can be produced from the dianhydride, which is known in the literature, or can be prepared by hydrogenation of the bicyclooctene dianhydride.

Crystallization of MCM-68 can be carried out at either static or stirred conditions in a suitable reactor vessel, such as for example, polypropylene jars or teflon lined or stainless steel autoclaves, at a temperature of 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time will vary with the nature of the reaction mixture employed and the crystallization conditions.

Synthesis of MCM-68 may be facilitated by the presence of at least 0.01 percent, preferably 0.10 percent and still more preferably 1 percent, seed crystals (based on total weight) of crystalline product.

Prior to its use in the process of the invention, the as-synthesized MCM-68 is subjected to treatment to remove part or all of any organic constituent. This is conveniently achieved performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product may then be converted into its active, hydrogen form, typically by the conventional steps of repeated ammonium exchange followed by calcination.

In its hydrogen form MCM-68 typically exhibits a high acid activity, with an alpha value of 900–1000. Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec-1). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395 (1980).

Prior to use in the process of the invention, particularly where feed comprises $C_{10}$+n-paraffins, it may be desirable to treat the MCM-68 to reduce its alpha activity to below 50 and more preferably to below 10. This is conveniently achieved by heating the crystalline material in the presence of steam at a temperature of 400 to 600° C. for 12 to 48 hours.

When used as a catalyst in the process of the invention, the MCM-68 will normally be incorporated with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides.

Naturally occurring clays which can be composited with the MCM-68 include the montmoillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to caldnation, acid treatment or chemical modification. Binders useful for compositing with the MCM-68 also include inorganic oxides, such as silica, zirconia, titania, magnesia, beryllia, alumina, and mixtures thereof.

In addition to the foregoing materials, the MCM-68 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of the MCM-68 crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The catalyst employed in the process of the invention preferably includes a hydrogenation component in intimate combination with the MCM-68. Examples of suitable hydrogenation components include tungsten, vanadium, molybdenum, rhenium, nickel, cobalt, chromium, manganese, or more preferably a noble metal such as platinum or palladium. Such component can be in the composition by way of cocrystallization, exchanged into the composition to the extent a Group IIIA element, e.g., aluminum, is in the structure, impregnated therein or intimately physically admixed therewith. In the case of platinum, impregnation can be effected by treating the MCM-68 with a solution containing a platinum-containing compound, such as chloroplatinic acid, platinous chloride and various compounds containing the platinum amine complex.

Preferably, the catalyst employed in the process of the invention contains from about 0.01% to about 5%, and more preferably from about 0.1% to about 2%, of hydrogenation component by weight of the total catalyst.

The process of the invention can be conducted on any paraffin-containing feedstock, although normally will be used with fuel and lube boiling-range feedstocks containing n-paraffins so as to isomerize the n-paraffins to more highly branched materials. Preferred feedstocks are those containing significant amounts of $C_4$ to $C_{20}$ n-paraffins. Examples of suitable fuel boiling-range feedstocks include gasoline boiling-range materials, such as straight-run gasoline and FCC gasoline, distillate boiling-range materials such as heavy cycle oil, light cycle oil, clarified slurry oil and other products of catalytic cracking. Examples of suitable lube boiling-range feedstocks are gas oils, such as coker heavy gas oils, vacuum gas oils, reduced crudes and atmospheric gas oils; as well as shale oils, tar sands, and waxes, including Fischer-Tropsch waxes and hydrocracked waxes.

The process of the invention can be conducted over a wide range of conditions including a temperature of about 200° C. to about 450° C., a pressure of about 200 to 3500 psig, a WHSV of about 0.1 $hr^{-1}$ to about 10 $hr^{-1}$, and a hydrogen/hydrocarbon mole ratio of about 0.5 to about 100. Preferably, said conditions include a temperature of about 250° C. to about 350° C., a pressure of about 300 to 3000 psig, a WHSV of about 0.4 $hr^{-1}$ to about 3 $hr^{-1}$, and a hydrogen/hydrocarbon mole ratio of about 1 to about 30. In general, lower temperatures in the ranges cited above are preferred with lighter n-paraffin feeds and higher temperatures are preferred with heavier n-paraffin feeds In order to more fully illustrate the nature of the invention and the manner of practicing same, the following examples are presented.

EXAMPLE 1

Synthesis of N,N'-Diethyl-exo,exo-bicyclo[2.2.2] oct-7-ene2,3:5,6-tetracarboxylic diimide.

To a 2000-ml 3-necked round-bottomed flask equipped with a magnetic stiring bar, a reflux condenser and a thermometer were attached. The flask was then charged with 70 wt % ethylamine in water (515.25 g, 8 moles) followed by exo,exo-bicyclo[2.2.2]oct-7-ene-2,3:5,6tetracarboxylic dianhydride (99.28 g, 0.4 moles) in portions along with vigorous stirring. After two hours of stirring at room temperature, water (300 ml) was added. The mixture was then stirred at 70° C. for 48 hours and then at 100° C. for 18 hours to drive off the excess amine. The reaction was then cooled to room temperature and the remaining ethylamine quenched with concentrated HCl in a dropwise fashion. The solid was then filtered under suction, washed with water (400 ml) and dried in a vacuum dessicator over drierite to give 120.90 g (100%) of diimide as white crystals.

Melting Point: 265–266° C.; NMR: Solvent=CDCl$_3$; $^{13}$C (δ/ppm): 12.846; 33.411; 33.776; 42.763; 130.685; 176.438. $^1$H(δ/ppm): 1.07 (6H, t); 2.97 (4H, s); 3.47 (4H, q4); 3.78 (2H, br.s); 6.10 (2H, t).

Combustion Analysis for C$_{16}$H$_{18}$N$_2$O$_4$

|  | % C | % H | % N |
|---|---|---|---|
| Calculated | 63.56 | 6.00 | 9.27 |
| Found | 63.45 | 6.00 | 9.21 |

EXAMPLE 2

Synthesis of N,N'-Diethyl-exo,exo-bicyclo[2.2.2]oct-7-ene-2,3:5,6-dipyrrolidine

All glassware in this procedure was dried in an oven at 150° C. for at least 12 hours. A 2000-ml, 3-necked round-bottomed flask equipped with a magnetic stirring bar, a thermometer and a graduated pressure equalized addition funnel sealed with a septum cap was comprehensively flushed with N$_2$. To this a soxhlet extractor with a thimble containing N,N'-diethyl-exo,exo-bicyclo[2.2.2]oct-7-ene-2,3:5,6-tetracarboxylic diimide (33.26 g, 110 mmol) topped with a reflux condenser and an inline gas bubbler was attached. The system was then charged with lithium aluminum hydride powder (12.52 g, 330 mmol) and anhydrous THF (1650 ml) via the addition funnel. After 24 hours of reflux to fully extract and deliver the diimide, the reaction was cooled to 5° C. Then the reaction was quenched with water (12.5 ml), 15% NaOH solution (12.5 ml) and water (37.6 ml) keeping the temperature below 10° C. After warming to room temperature and suction filtration of the solids followed by washing with dichloromethane (660 ml), water (220 ml) was added to the combined filtrates which were then acidified using conc. HCl to pH=1–2. The organic layer was then separated, water (220 ml) added and the pH adjusted to 1–2 with concentrated HCl. This aqueous layer was separated and combined with the previous aqueous fraction, rendered basic with 50% NaOH solution to pH=11–12 and extracted with dichloromethane (5×275 ml). These combined organic fractions were dried over Na$_2$SO$_4$, filtered and evaporated in vacuum to give a yellow/orange oil which may solidify upon cooling (22.56 g, 83%). The oil was extracted with ether (2×150 mL), the fractions being filtered, combined, dried over Na$_2$SO$_4$, re-filtered & the solvent evaporated under vacuum to give a gold oil which solidifies upon cooling (20.15 g, 74%). $^1$H and $^{13}$C NMR analysis of the crude yellow solid showed no visible impurities and the diamine was used in this form in the subsequent diiodide preparation. However, an analytical sample of the diamine was obtained by vacuum distillation of the yellow solid (10 mTorr, 106–110° C.) to give a clear oil (52% efficiency) which crystallizes to a white solid on cooling.

Melting Point: 57–58° C.; NMR: Solvent=CDCl$_3$; $^{13}$C (δ/ppm): 13.837; 35.491; 44.210; 49.831; 58.423; 135.294. $^1$H(δ/ppm): 1.05 (6H, t); 1.85 (4H, t); 2.37 (4H, q4); 2.49 (6H, br.d); 3.04 (4H, t); 6.07 (2H, t).

Combustion Analysis for C$_{16}$H$_{26}$N$_2$

|  | % C | % H | % N |
|---|---|---|---|
| Calculated | 77.99 | 10.64 | 11.37 |
| Found | 77.82 | 10.59 | 11.31 |

EXAMPLE 3

Synthesis of N,N,N',N'-Tetraethyl-exo,exo-bicyclo[2.2.2]oct-7-ene-2,3:5,6-dipyrrolidinium diiodide (Bicyclodiquat-Et$_4$ 2I)

To a 1000ml 3-necked round-bottomed flask equipped with a magnetic stirring bar, a reflux condenser, a thermometer and a pressure equalized addition funnel containing a solution of iodoethane (67.37 g, 432 mmol) in ethanol (216 ml) were attached. The flask was then charged with N,N'-diethyl-exo,exo-bicyclo[2.2.2]oct-7-ene-2,3:5,6-dipyrrolidine (35.48 g, 144 mmol) and ethanol (144 ml). After stirring until all the solids had dissolved the iodoethane solution was added slowly and the mixture refluxed overnight. After subsequent cooling to 10° C., the solids were suction filtered and washed with acetone (144 ml). The resultant off-white solid was then refluxed in acetone (500 ml) for 15 minutes, suction filtered and dried in a vacuum dessicator over drierite to give a tan solid, 70.78 g (88%).

Melting Point: >270° C. (decomposition); NMR: Solvent=D$_2$O; $^{13}$C (δ/ppm): 10.115; 10.932; 35.721; 42.597; 55.604; 58.370; 67.030; 130.870. $^1$H(δ/ppm): 1.28 (12H, t); 2.85 (8H, br.s); 2.92 (2H, br.s); 3.32 (8H, q6); 3.81 (4H, d); 6.45 (2H, t).

Combustion Analysis for C$_{20}$H$_{36}$N$_2$I$_2$

|  | % C | % H | % N |
|---|---|---|---|
| Calculated | 43.02 | 6.50 | 5.02 |
| Found | 43.19 | 6.58 | 4.85 |

EXAMPLE 4

Synthesis of Aluminosilicate MCM-68

14 g of Colloidal Silica Sol (30 wt % of SiO$_2$: Aldrich Ludox SM-30), and 22.096 g of distilled water are mixed with 0.6056 g of Al(OH)$_3$ (Aluminum Hydroxide, solid). To this reaction mixture added 7.354 g of KOH (88.8% purity) (Potassium Hydroxide, 20 wt% solution) and then added 3.912 g of Bicyclodiqaut-Et$_4$ 2I$^-$ (N,N,N',N'-Tetraethyl-exo,exo-bicyclo[2.2.2]oct-7-ene-2,3:5,6dipyrrolidinium diiodide, solid). The reaction can be represented by the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$2I/Si | 0.10 |

The combined mixture was added to an autoclave and heated to 160° C. for 300 hours unstirred. The product was then filtered and washed with water and dried overnight under an IR lamp. The solid is subsequently calcined in air at a temperature of 540° C. for 8 hours to yield the material designated as MCM-68. The powder diffraction peaks for the as-synthesized and calined samples collected using a synchrotron source are shown in FIGS. 1 and 2.

EXAMPLE 5

Ammonium Exchange and Preparation of H-MCM68

The calcined MCM68 material from Example 4 was ion exchanged 4 four times with a 1M ammonium nitrate solution at 80° C. then filtered washed and dried under an IR lamp. Subsequently it was calcined at 540° C. in air for 8 hrs. The H-MCM-68 obtained had an alpha value of a 1000.

EXAMPLE 6

Synthesis of Aluminosilicate MCM-68

7 g of Colloidal Silica (30 wt %), Al(OH)$_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6dipyrrolidinium diiodide, solid) and distilled water were combined in the following mole ratios:

| | |
|---|---|
| Si/Al$_2$ | 30 |
| H$_2$O/Si | 30 |
| OH/Si | 0.375 |
| K$^+$/Si | 0.375 |
| Bicyclodiquat-Et$_4$2I/Si | 0.10 |

The combined mixture was added to an autoclave and heated to 160° C. for 150 hours. The product was then filtered and washed with water and dried overnight under an IR lamp. The solid was subsequently calcined in air at a temperature of 540° C. for 8 hours to yield the MCM-68. The powder x-ray diffraction of the final product showed the presence of trace amounts of zeolite ZSM-12.

EXAMPLE 7

Synthesis of Aluminosilicate MCM68

7 g of Colloidal Silica (30 wt %), Al(OH)$_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6dipyrrolidinium diiodide, solid) and distilled water were combined in the following mole ratios:

| | |
|---|---|
| Si/Al$_2$ | 15 |
| H$_2$O/Si | 30 |
| OH/Si | 0.375 |
| K$^+$/Si | 0.375 |
| Bicyclodiquat-Et$_4$2I/Si | 0.10 |

The combined mixture was added to an autoclave and heated to 160° C. for 240 hours. The product was then filtered and washed with water and dried overnight under an IR lamp. The solid was subsequently calcined in air at a temperature of 540° C. for 8 hours to yield MCM-68. The powder x-ray diffraction of the final product indicated the presence of trace amounts of zeolite Beta.

EXAMPLE 8

Synthesis of Aluminosilicate MCM68

14 g of Colloidal Silica (30 wt %), Al(OH)$_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$2I/Si | 0.10 |

The combined mixture was added to an autoclave and heated to 170° C. for 200 hours at 200 rpm. The product was then filtered and washed with water and dried overnight under an IR lamp. The solid was subsequently calcined in air at a temperature of 540° C. for 8 hours to yield MCM-68.

EXAMPLE 9

Synthesis of Aluminosilicate MCM-68 with 2 wt. % seeds of as-synthesized MCM-68.

7 g of Colloidal Silica (30 wt %), Al(OH)$_3$ (Aluminum Hydroxide, solid), KOH (Potassium Hydroxide, 20 wt % solution), Bicydodiqaut-Et$_4$ 2I (N,N,N',N'-Tetraethyl-exosexo-bicyclo[2.2.2]oct-7-ene-2,3:5,6-dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$2I/Si | 0.10 |

To this mixture were added 2 wt. % seed crystals of as-synthesized MCM-68 from Example 5. The combined mixture was added to an autoclave and heated to 160° C. for 200 hours. The product was then filtered and washed with water and dried overnight under an IR lamp. The solid was subsequently calcined in air at a temperature of 540° C. for 8 hours to yield the material designated as MCM-68.

EXAMPLE 10

1.0 gram of calcined MCM-68 crystal produced in Example 5 was combined with 0.73 grams of LaRoche Versal 300 alumina (% solids=73.0) and pelleted in a hydraulic press. After pelleting, the alumina bound MCM-68 crystal was calcined in an open dish in static air for 3 hours at 1000° F. (540° C.). After calcination, the alumina-bound MCM-68 was impregnated with platinum tetraammine nitrate (0.6 wt % Pt) using incipient wetness. After Pt impregnation, the material was dried at 250OF (120° C.) overnight followed by calcination in bone-dry air for 3 hours at 680° F. (360° C.).

The resultant PtMCM-68 catalyst was then tested in the hydroisomerization of decane by loading 1 gram of the catalyst sized to 14/25-mesh into a glass reactor fitted with an imbedded thermocouple/well. The catalyst was initially dried at 500° F. (260° C.) for 3 hours in 100 sccm $N_2$. After drying, the catalyst was reduced at 500° F. (260° C.) for 3 hours in 100 sccm $H_2$. Normal decane was then fed downflow through the reactor with $H_2$ as carrier gas. The $H_2$ to hydrocarbon molar ratio was 100 with a 0.4 WHSV decane flow. The reaction was carried out in a temperature range of 325° F. (163° C.) to 495° F.(257° C.). Products were analyzed on a Hewlett Packard 5990 gas chromatograph equipped with a 150M-fused silica capillary identified as DB1™ and the results are summarized in Table 3.

TABLE 3

| Temp., ° F. | 325 | 350 | 375 | 400 | 425 | 450 | 475 | 485 | 495 |
|---|---|---|---|---|---|---|---|---|---|
| n-C10 Conversion | 26 | 75 | 100 | 100 | 100 | 100 | 100 | 100 | 100 |
| Yields, wt % | | | | | | | | | |
| Iso-C10 | 17.1 | 31.8 | 0 | 0 | 0 | 0 | 0 | 0 | 0 |
| Iso-C9 | 0.2 | 0.9 | 0 | 0 | 0 | 0 | 0 | 0 | 0 |
| Iso-C8 | 0 | 0 | 0 | 0 | 0 | 0 | 0 | 0 | 0 |
| Iso-C7 | 0.5 | 3.4 | 5.0 | 1.7 | 0 | 0 | 0 | 0 | 0 |
| Iso-C6 | 2.1 | 11.1 | 24.2 | 23.7 | 23.1 | 23.8 | 12.5 | 11.1 | 15.9 |
| Iso-C5 | 2.0 | 11.0 | 26.4 | 24.1 | 23.6 | 22.9 | 21.1 | 26.2 | 24.9 |
| IsoC4 | 1.4 | 7.5 | 18.9 | 21.5 | 21.2 | 17.0 | 28.4 | 24.0 | 17.2 |
| Ratios | | | | | | | | | |
| 5-MN/2-MN | 0.7 | 0.9 | | | | | | | |
| 4-MN/2-MN | 1.2 | 1.6 | | | | | | | |
| 3-MN/2-MN | 1.4 | 1.7 | | | | | | | |

EXAMPLE 11

In a small horizontal tube furnace, MCM-68 produced as in Example 5 was steamed for 4 hours at 1382° F (750° C.) in 100% steam. After steaming, the alpha activity of the zeolite was 6.5. The steamed MCM-68 crystal, 1.268 grams, was combined with 0.993 grams of LaRoche Versal 300 alumina (% solids=68.8) and pelleted in a hydraulic press. After pelleting, the alumina-bound MCM-68 crystal was calcined in an open dish in static air for 3 hours at 1000° F. (540° C.). The calcined, alumina-bound MCM-68 was then impregnated with platinum tetraammine nitrate (0.6 wt % Pt) using incipient wetness. After Pt impregnation, the material was dried at 250° F.(120° C.) overnight followed by calcination in bone-dry air for 3 hours at 680° F. (360° C.).

The resultant steamed PtMCM-68 catalyst was then tested in the hydroisomerization of decane in Example 11 and the results are summarized in Table 4.

EXAMPLE 12

The calcined MCM-68 of Example 4 was extruded with Versal 300 alumina (65%/35% by weight MCM-68/Versal 300 alumina) at 51% solids and dried overnight at 250° F. (120° C.). The resulting catalyst was exchanged twice with 1 N NH4NO3 at ambient temperature and calcined in air at 1000° F. (540° C.) for 3 hours. The resulting material was exchanged 4 times with 1 N $NH_4NO_3$, 2 hours each at 80° C. while controlling the pH at 7.0. This was followed by further air calcination at 1000° F. (540° C.) for 12 hours and at 1100° F. (590° C.) for 6 hours. The resulting base material had an alpha value of 300.

Two catalysts were prepared from this material. The first catalyst, Catalyst A, was prepared by steaming the base material first at 1000° F. (540° C.) for 24 hours and then at 1150° F. (620° C.) for an additional 8 hours. The resulting material had an alpha value of 4 and was impregnated by the incipient wetness technique with approximately 1 wt % platinum using platinum tetraamine nitrate, dried at 250° F. (120° C.) and calcined in 5v/v/min air at 680° F. (360° C.) for one hour. The second catalyst, Catalyst B, was prepared by subjecting the base material to an overnight competitive exchange with platinum tetraamine nitrate in 1 N $NH_4NO_3$, drying at 250° F. (120° C.) and calcining at 680° F.(360° C.) for one hour and then at 740° F. (390° C.) for a second hour.

Each of the resultant catalysts was then separately tested for the hydroisomerization of hexadecane (99% $nC_6$) obtained from Aldrich Chemical and used as received.

TABLE 4

| Temp., ° F. | 325 | 350 | 375 | 400 | 425 | 450 | 475 | 485 | 495 |
|---|---|---|---|---|---|---|---|---|---|
| n-C10 Conversion | 0.3 | 0.3 | 0.9 | 2.5 | 7.8 | 23.0 | 57.8 | 73.0 | 86.8 |
| Yields, wt % | 0.3 | 0.3 | 0.9 | 2.2 | 7.0 | 21.1 | 52.2 | 62.4 | 67.3 |
| Iso-C10 | | | | | | | | | |
| Iso-C9 | 0 | 0 | 0 | 0 | 0 | 0 | 0 | 0 | 1.4 |
| Iso-C8 | 0 | 0 | 0 | 0 | 0 | 0 | 0 | 0 | 0 |
| Iso-C7 | 0 | 0 | 0 | 0 | 0 | 0 | 0.4 | 0.6 | 1.2 |
| Iso-C6 | 0 | 0 | 0 | 0 | 0 | 0.1 | 0.7 | 1.5 | 3.0 |
| Iso-C5 | 0 | 0 | 0 | 0 | 0 | 0.1 | 0.7 | 1.5 | 3.0 |
| IsoC4 | 0 | 0 | 0 | 0 | 0 | 0.1 | 0.5 | 1.1 | 2.3 |
| Ratios | | | | | | | | | |
| 5-MN/2-MN | | | 0.7 | 0.7 | 0.7 | 0.6 | 0.5 | 0.5 | 0.5 |
| 4-MN/2-MN | | | 1.3 | 1.3 | 1.3 | 1.2 | 1.0 | 1.0 | 1.0 |
| 3-MN/2-MN | | | 2.5 | 1.7 | 1.4 | 1.3 | 1.2 | 1.2 | 1.2 |

About 10 cc of each catalyst extrudate was sized to a length/diameter ratio of about 1 and was loaded into a tubular reactor with 3 cc of 80/120 mesh sand to fill the void fraction. The catalyst was dried in nitrogen and treated in hydrogen at 250° C. (120° C.) for two hours and then pretreated using hydrogen sulfide (2% in hydrogen) while increasing the temperature to 370° C., prior to pressurizing to 600 psig and flooding the catalyst bed with hexadecane feed at 2–4 LHSV. The feed rate was then adjusted to give 0.5 LHSV and temperature was adjusted to give desired conversion levels. Hydrogen flow was maintained at about 6000 scf/bbl (~15 moles $H_2$/mole $nC_{16}$).

Table 5 summarizes the acid and metal contents of the two catalysts and the results obtained for hexadecane hydroisomerization. The isomer yield is defined as the weight % of n-hexadecane that is converted to branched C16 isomers.

TABLE 5

| Catalyst | A | B |
|---|---|---|
| Alpha | 4 | 300 |
| Platinum loading, wt % | 1.1 | 1.0 |
| Maximum yield of iC16 isomers, wt % | 63 | 12 |
| Temperature required for 95% nC16 conversion, ° F. | 575 | 430 |

Table 6 illustrates the yield obtained at various conversion levels for Catalyst A.

TABLE 6

| n-C16 Conversion, % | Isomer Yield, wt % |
|---|---|
| 12.5 | 11.3 |
| 13.2 | 11.8 |
| 17.2 | 14.9 |
| 25.2 | 21.6 |
| 39.2 | 33.2 |
| 60.3 | 48.2 |
| 66.8 | 55.0 |
| 81.0 | 59.3 |
| 85.1 | 63.3 |
| 91.8 | 59.6 |
| 94.7 | 59.5 |
| 98.9 | 49.3 |
| 98.9 | 52.2 |
| 99.2 | 49.4 |

Table 7 illustrates the yield obtained at various conversion levels for Catalyst B.

TABLE 7

| n-C16 Conversion, % | Isomer Yield, wt % |
|---|---|
| 2.8 | 1.0 |
| 47.6 | 11.4 |
| 70.0 | 12.2 |
| 99.0 | 0.8 |
| 100.0 | 0.1 |

The data in Tables 6 and 7 show that steaming the catalyst to an alpha value of 4 improves the performance of the catalyst, leading to a higher yield of $C_{16}$ isomers at any given $nC_{16}$ conversion.

EXAMPLE 13

The Pt-containing MCM-68 Catalyst B from Example 12 was compared for use in the isomerization of n-pentane with platinum-containing zeolite beta and mordenite catalysts (containing equivalent Pt loadings) and with a commercial Pt mordenite catalyst (containing 0.4% by weight Pt).

Catalytic testing was performed in an isothermal, fixed-bed reactor. Feeds were delivered using a syringe pump for normal pentane and a mass flow controller for hydrogen, pressure was maintained through a back pressure regulator at 350 psig. All materials were compared on a WHSV (weighted hourly space velocity) basis. Reactor conditions are shown in Table 8 below.

In each case, the catalyst material was in extrudate form and sized to 14/30 mesh. The catalyst was mixed with an equal volume of 50/70 mesh sand to fill any voids to prevent channeling in the reactor bed. The catalyst bed was sandwiched in between >40 mesh sand beds with an ample pre-heating zone upstream of the catalyst to assure proper feed temperature on contact. The catalyst and sand beds were isolated with plugs of quartz wool.

Each catalyst was pretreated by ramping to 300° C. over three hours under hydrogen flow (116 cc/min. @ 1 atm), held for 3 hours at 300° C., then cooled to 240° C., at which point feed was introduced. After a brief lineout period, the reactor temperature was increased to the first set of test conditions.

The comparative pentane isomerization performance of MCM-68, zeolite beta, and both laboratory-prepared and commercial mordenite catalysts at identical reactor conditions is shown in Table 8 below.

TABLE 8

| Catalyst | | | | | | | | | | | | |
|---|---|---|---|---|---|---|---|---|---|---|---|---|
| type | Pt/MCM-68 | | | Pt/Beta | | Pt/MOR | | Pt/MOR (commercial) | | | | |
| wt % Pt | 0.83 | | | 0.84 | | 0.8 | | 0.39 | | | | |
| Conditions | | | | | | | | | | | | |
| temp. C. | 260 | 260 | 270 | 260 | 270 | 260 | 270 | 260 | 260 | 260 | 270 | 270 |
| PSIG | 350 | 350 | 350 | 350 | 350 | 350 | 350 | 350 | 350 | 350 | 350 | 350 |
| H2:HC | 2 | 1 | 1 | 2 | 1 | 2 | 1 | 2 | 1 | 2 | 2 | 1 |
| WHSV | 1.8 | 1.8 | 1.8 | 1.8 | 1.8 | 1.8 | 1.8 | 1.8 | 1.8 | 1.8 | 1.8 | 1.8 |
| LHSV | 1.7 | 1.7 | 1.7 | 1.7 | 1.7 | 1.7 | 1.7 | 2 | 2 | 2.1 | 2.1 | 2.1 |
| GC area % | | | | | | | | | | | | |
| C1–C3 | 0.25 | 0.31 | 0.52 | 0.19 | 0.56 | 0.44 | 0.83 | 0.22 | 0.23 | 0.18 | 0.31 | 0.38 |
| iso-C4 | 0.07 | 0.13 | 0.31 | 0.02 | 0.18 | 0.11 | 0.57 | 0.17 | 0.24 | 0.09 | 0.25 | 0.52 |
| n-C4 | 0.21 | 0.27 | 0.45 | 0.15 | 0.49 | 0.21 | 0.54 | 0.15 | 0.18 | 0.14 | 0.28 | 0.36 |
| iso-C5 | 58 | 63 | 67.6 | 35.1 | 60 | 49.8 | 65.5 | 59.4 | 63.9 | 59.2 | 65.9 | 67.1 |

TABLE 8-continued

| | | | | | | | | | | | | |
|---|---|---|---|---|---|---|---|---|---|---|---|---|
| n-C5 | 41.3 | 36.1 | 30.7 | 64.4 | 38.5 | 49.2 | 31.7 | 39.7 | 35 | 39.6 | 32.5 | 30.5 |
| % C4 | 0.53 | 0.71 | 1.28 | 0.36 | 1.23 | 0.76 | 1.94 | 0.54 | 0.65 | 0.41 | 0.84 | 1.26 |
| % I/(l + n) | 58.4 | 63.6 | 68.7 | 35.3 | 60.9 | 50.3 | 67.4 | 59.9 | 64.6 | 59.9 | 67.0 | 68.8 |
| % C5 conv. | 58.7 | 63.9 | 69.3 | 35.6 | 61.5 | 50.8 | 68.3 | 60.3 | 65.0 | 60.4 | 67.5 | 69.5 |
| %sel. iso-C5 | 98.8 | 98.6 | 97.5 | 98.6 | 97.6 | 98.0 | 96.0 | 98.6 | 98.3 | 98.0 | 97.5 | 96.5 |

The above data indicates that at 270° C., the Pt/MCM-68 and both Pt/mordenite catalysts have equivalent isopentane selectivity and pentane conversion, but with the 0.8% Pt/mordenite catalyst exhibiting a significantly higher yield of cracked products. At 260° C., the Pt/MCM-68 catalyst retains equivalent performance to the commercial catalyst, whereas the 0.8% Pt/mordenite is ~14% less active. By comparison, zeolite beta with the same Pt loading and similar acidity (alpha), has equal isopentane selectivity to the other two catalysts, but considerably less overall pentane conversion at both of the reaction temperatures studied.

It will be seen decreasing the Pt loading of the mordenite catalyst to 0.4% resulted in greatly reduced conversion and extent of isomerization (i-pentane/i-pentane+n-pentane= 33% and 57% at 260° and 270°, respectively).

What is claimed is:

1. A process for isomerizing paraffins comprising the step of contacting a feed containing paraffins with a catalyst comprising a synthetic porous crystalline material which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

2. The process of claim 1 wherein said porous crystalline material contains one 12-membered ring channel system and two 10-membered ring channel systems.

3. The process of claim 2 in which the channels in each 10-membered ring channel system of crystalline material extend in a direction generally perpendicular to the channels in the other 10-membered ring channel system and to the channels in the 12-membered ring channel system.

4. A process for isomerizing paraffins comprising the step of contacting a feed containing paraffins with a catalyst comprising a synthetic porous crystalline material characterized by an X-ray diffraction pattern including values substantially as set forth in Table I of the specification and having a composition comprising the molar relationship

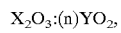

$$X_2O_3:(n)YO_2,$$

wherein n is at least about 5, X is a trivalent element, and Y is a tetravalent element.

5. The process of claim 4 wherein X is a trivalent element selected from the group consisting of boron, iron, indium, gallium, aluminum, and a combination thereof; and Y is a tetravalent element selected from the group consisting of silicon, tin, titanium, germanium, and a combination thereof.

6. The process of claim 4 wherein X comprises aluminum and Y comprises silicon.

7. The process of claim 4 wherein said catalyst also contains a hydrogenation metal.

8. The process of claim 4 wherein said catalyst has an alpha value below 50.

9. The process of claim 4 wherein said catalyst has an alpha value below 10.

10. The process of claim 4 wherein said contacting step is effected at a temperature of about 200° C. to about 450° C., a pressure of about 200 to 3500 psig, a WHSV of about 0.1 hr$^{-1}$ to about 10 hr$^{-1}$, and a hydrogen/hydrocarbon mole ratio of about 2 to about 100.

* * * * *